(12) United States Patent
Villarreal

(10) Patent No.: US 10,406,039 B2
(45) Date of Patent: Sep. 10, 2019

(54) MALE INCONTINENCE PAD

(71) Applicant: Vivian Louise Villarreal, Edinburg, TX (US)

(72) Inventor: Vivian Louise Villarreal, Edinburg, TX (US)

(*) Notice: Subject to any disclaimer, the term of this patent is extended or adjusted under 35 U.S.C. 154(b) by 606 days.

(21) Appl. No.: 15/165,774

(22) Filed: May 26, 2016

(65) Prior Publication Data

US 2016/0346137 A1 Dec. 1, 2016

Related U.S. Application Data

(60) Provisional application No. 62/166,486, filed on May 26, 2015.

(51) Int. Cl.

| | | |
|---|---|---|
| *A61F 5/453* | (2006.01) | |
| *A61F 13/42* | (2006.01) | |
| *A61F 13/471* | (2006.01) | |
| *A61F 13/537* | (2006.01) | |
| *A61F 13/47* | (2006.01) | |
| *A61F 5/44* | (2006.01) | |

(52) U.S. Cl.
CPC .......... *A61F 13/471* (2013.01); *A61F 5/4401* (2013.01); *A61F 5/453* (2013.01); *A61F 13/42* (2013.01); *A61F 13/4704* (2013.01); *A61F 13/53743* (2013.01)

(58) Field of Classification Search
CPC .......... A61F 5/44; A61F 5/4401; A61F 5/451; A61F 5/453; A61F 2005/4402; A61F 13/471; A61F 13/4915; A61F 13/42
USPC .................................................. 604/385.09
See application file for complete search history.

(56) References Cited

U.S. PATENT DOCUMENTS

| | | | | |
|---|---|---|---|---|
| 4,886,509 A | * | 12/1989 | Mattsson | A61F 5/4401 604/349 |
| 5,910,137 A | | 6/1999 | Clark et al. | |
| 6,105,174 A | * | 8/2000 | Nygren | A61F 13/471 2/400 |
| 6,129,719 A | * | 10/2000 | Nozaki | A61F 13/471 604/385.01 |
| 6,336,919 B1 | * | 1/2002 | Davis | A61F 5/453 604/346 |
| 6,530,909 B1 | * | 3/2003 | Nozaki | A61F 13/471 604/349 |
| 6,569,135 B1 | * | 5/2003 | Mula | A61F 13/471 604/347 |

(Continued)

OTHER PUBLICATIONS

International Search Report, dated Sep. 2, 2016, PCT Patent Application No. PCT/US16/34375, Int. Filing Date: May 26, 2016.

(Continued)

*Primary Examiner* — Catharine L Anderson
(74) *Attorney, Agent, or Firm* — Smith Brandenburg Ltd.

(57) ABSTRACT

Male incontinence pads may be formed and used by a variety of techniques. In particular implementations, a male incontinence pad may include a first absorbent pad, a second absorbent pad, and a water impermeable lining. The water impermeable lining may be between the pads, and the first absorbent pad, the second absorbent pad, and the lining may each include an aperture that are aligned to allow a male member to be placed therethrough. The second absorbent pad may be adapted to be folded to form a pocket for the male member.

9 Claims, 11 Drawing Sheets

(56) References Cited

U.S. PATENT DOCUMENTS

2011/0015604 A1 6/2011 Back
2012/0308787 A1 12/2012 Kozee et al.

OTHER PUBLICATIONS

Written Opinion of Int. Search Authority, dated Sep. 2, 2016, PCT Patent Application No. PVT?US16/34375, Int. Filing Date: May 26, 2016.

* cited by examiner

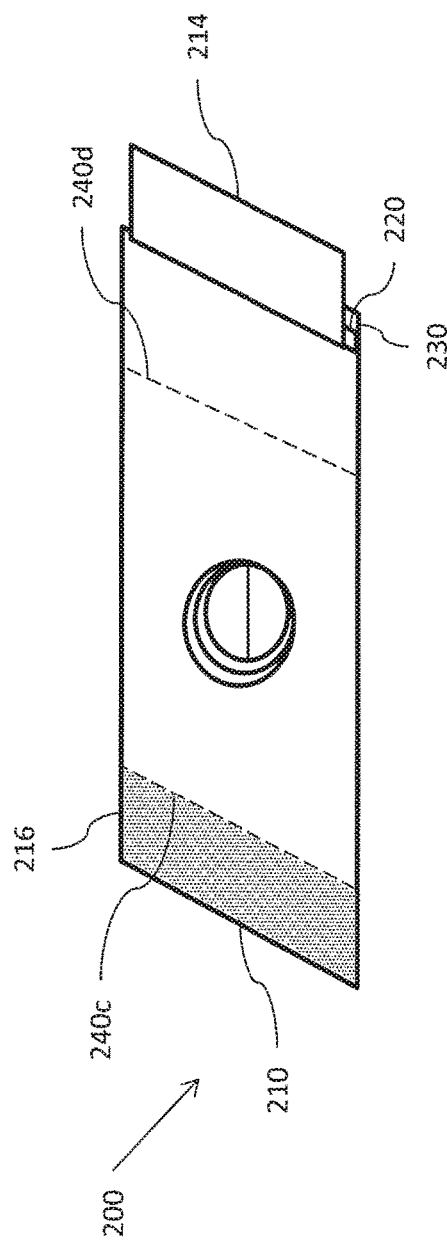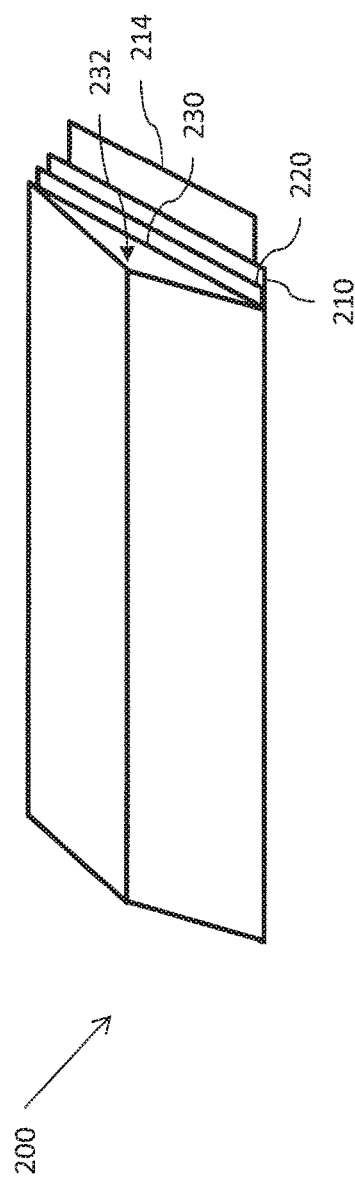
FIG. 2C
FIG. 2C'

MALE INCONTINENCE PAD

RELATED APPLICATIONS

This application claims priority to and the benefit of U.S. Patent Application No. 62/166,486, filed May 26, 2015. This prior application is herein incorporated by reference in its entirety.

BACKGROUND OF THE INVENTION

Adult humans can become paralyzed due to a variety of reasons (e.g., falls, car accidents, gunshots, etc.). For example, there are between 250,000 and 350,000 people living in the United States with spinal cord injuries, and there are approximately 12,000 new cases each year. Improved emergency care for people with spinal cord injuries and aggressive treatment and rehabilitation can minimize damage to the nervous system and even restore some function to the patient.

Spinal cord injury primarily affects young adults. The average age of injury is 41 years old, and over 80% of spinal cord injuries occur among males.

For people dealing with paralysis in the lower part of their body, managing the discharge of bodily waste is typically a constant issue. Often, such people wear adult-sized incontinence briefs, which can be changed when they are soiled.

SUMMARY

Male incontinence pads may be formed and used by a variety of techniques. In particular implementations, a male incontinence pad may include a first absorbent pad, a second absorbent pad, and a water impermeable lining. The water impermeable lining may be between the pads, and the first absorbent pad, the second absorbent pad, and the lining may each include an aperture that are aligned to allow a male member to be placed therethrough. The second absorbent pad may be adapted to be folded to form a pocket for the male member.

One or more male incontinence pads may have one or more features. For example, a pad may be able to substantially (or maybe even completely) absorb discharge from a wearer. Thus, when it is time to tend to the wearer, the task is much easier, as the pad may be removed simply and only minimal cleanup around the male member may be required. Moreover, a new pad may be readily fitted. When a wearer only uses a full-size incontinence brief, the entire brief must be changed, which requires a substantial amount of physical effort. Moreover, for individuals that require regular hydration (e.g., through a IV), this may mean that they need to be tended to every few hours. Having to change a full-size brief every few hours is a very labor intensive task. Additionally, the pad may prevent bed sores in the groin area due to the fact that the patient would not have to lie wet with urine for long periods of time in the region surrounding the entire groin area. This is especially true if the pad is being changed frequently, as it should be, which may be more likely since the changing process is greatly simplified. Moreover, the pad may cost quite a bit less than a typical incontinence brief, which may save the caregiver money.

A variety of other features will be apparent to one of skill in the art from the following description, the figures, and the claims.

BRIEF DESCRIPTION OF THE DRAWINGS

FIG. 2C is a line drawing illustrating the second example male incontinence pad at an additional step of operation.

FIG. 2C' is a line drawing illustrating the reverse side of the pad in FIG. 2C.

DETAILED DESCRIPTION

Figure 1A:
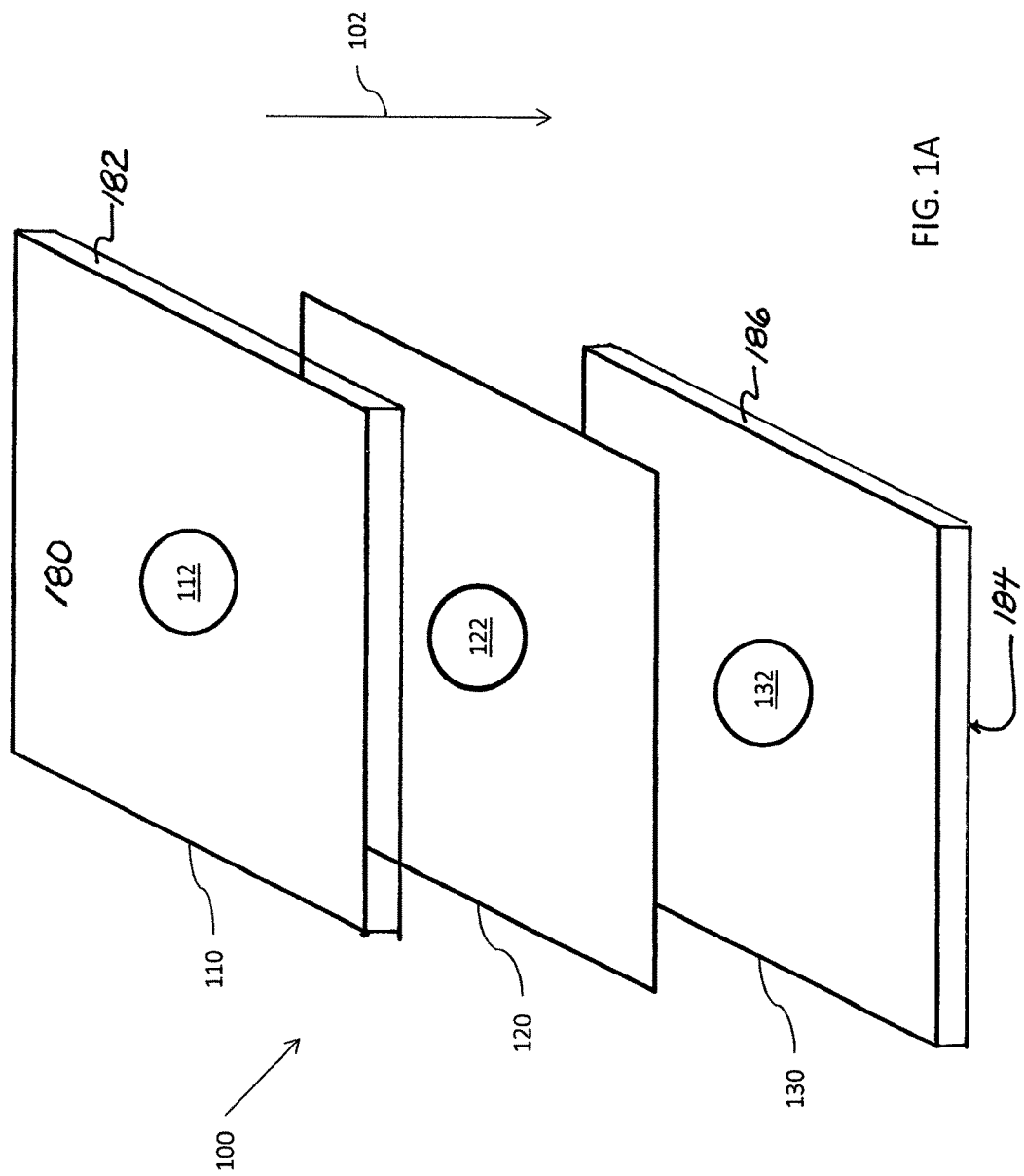
FIG. 1A is a line drawing illustrating an exploded view of an example male incontinence pad.
Figure 1B:
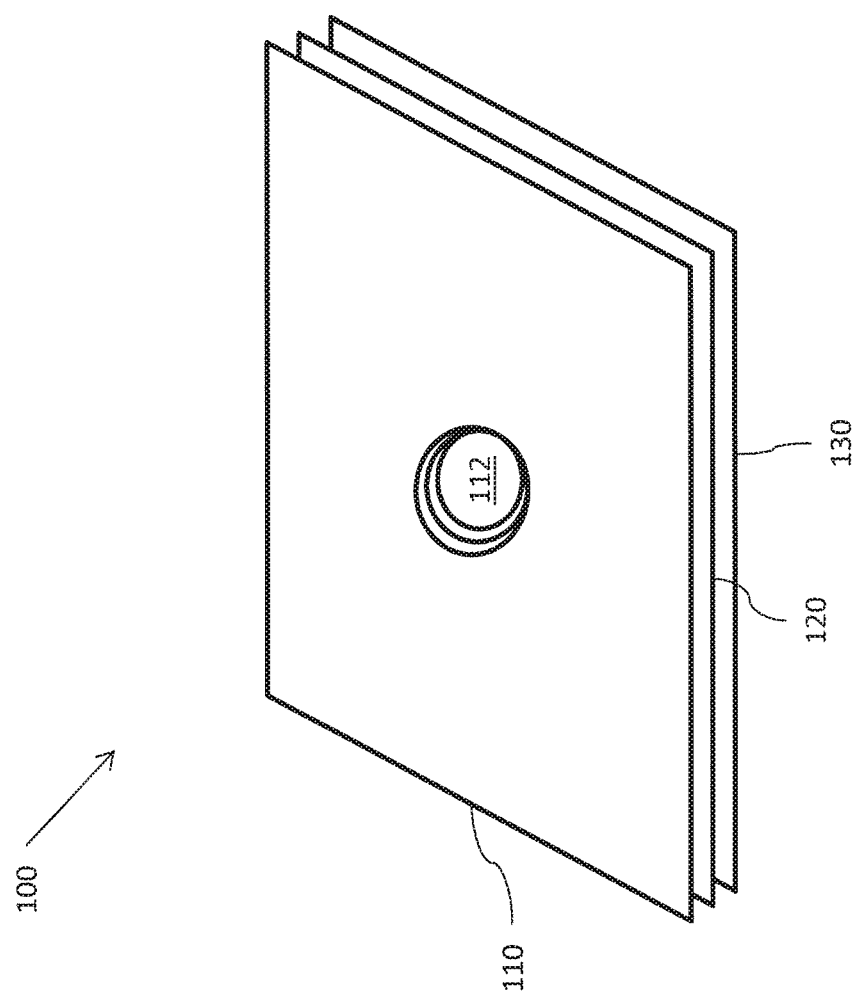
FIG. 1B is a line drawing illustrating a partially assembled view of the example male incontinence pad.
Figure 2A:
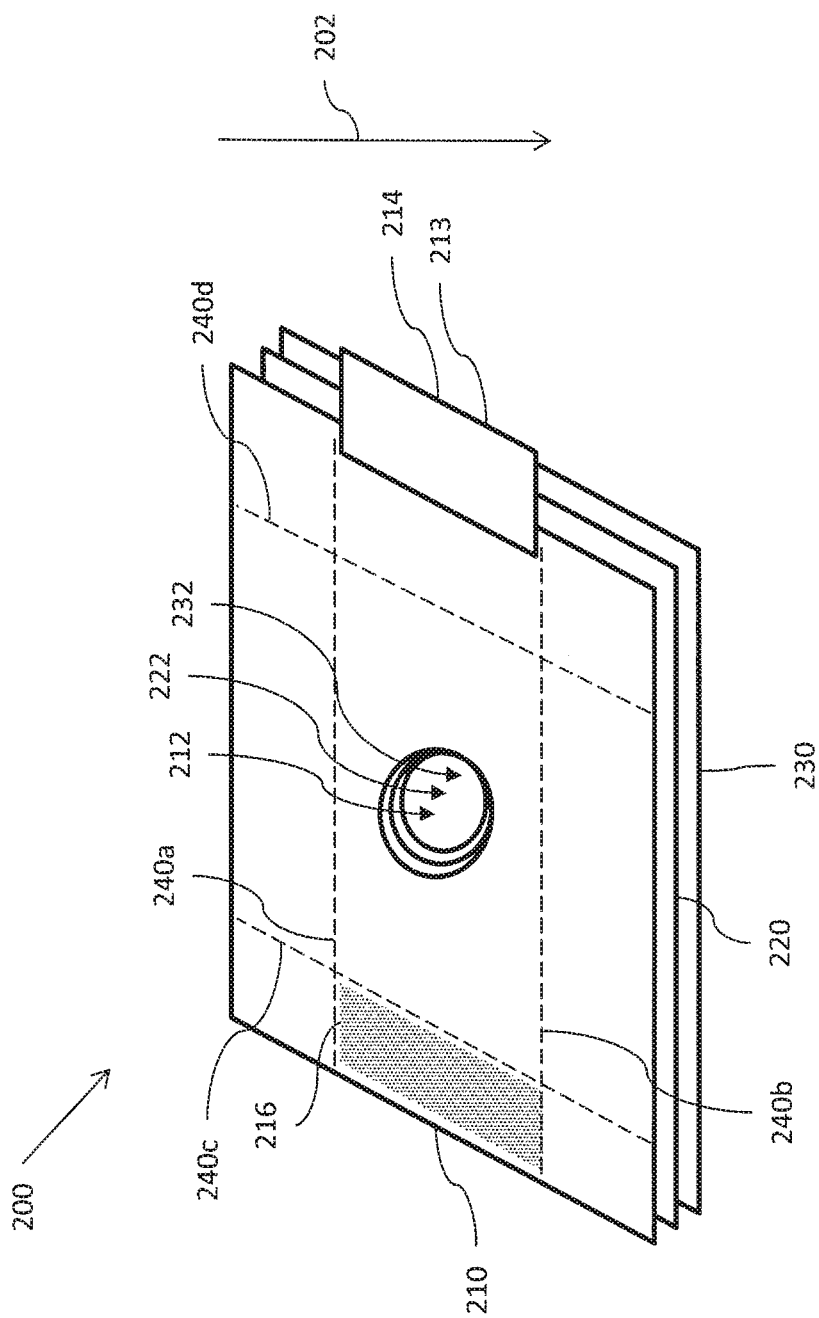
FIG. 2A is a line drawing illustrating a second example male incontinence pad at one step of operation.
Figure 2B:
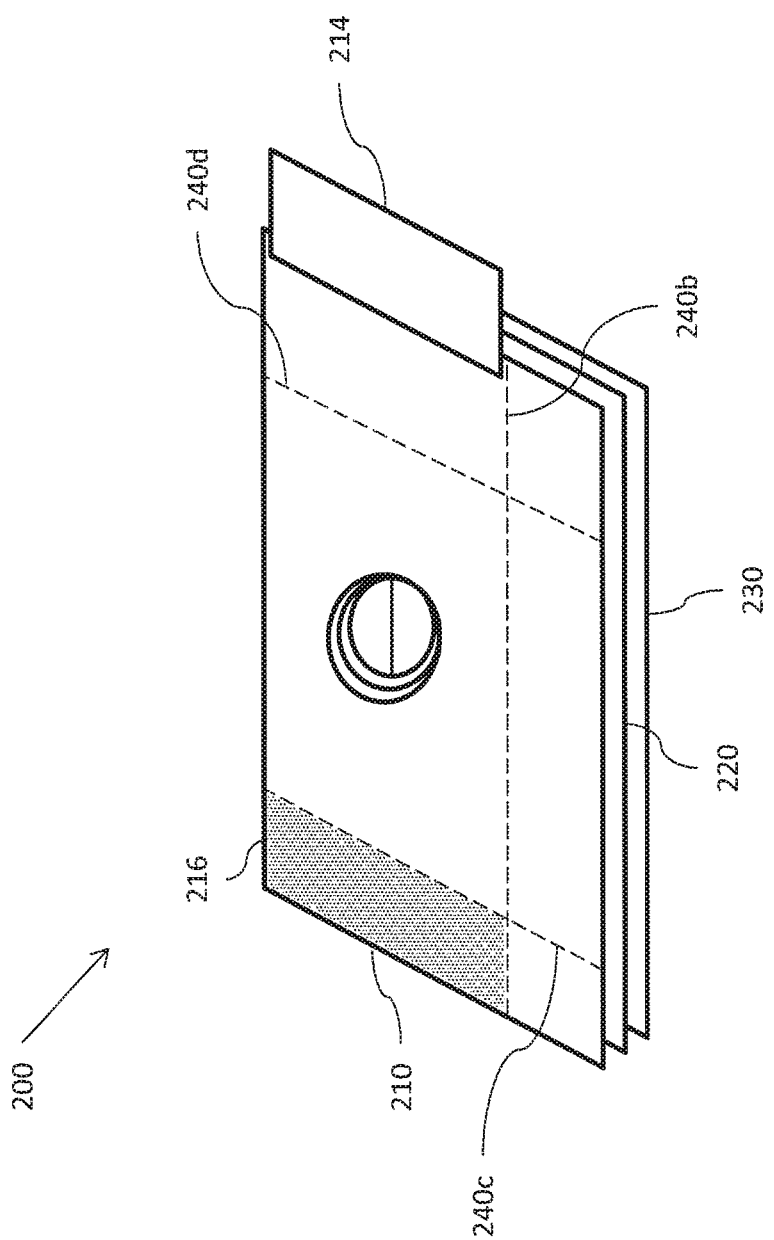
FIG. 2B is a line drawing illustrating the second example male incontinence pad at another step of operation.
Figure 2D:
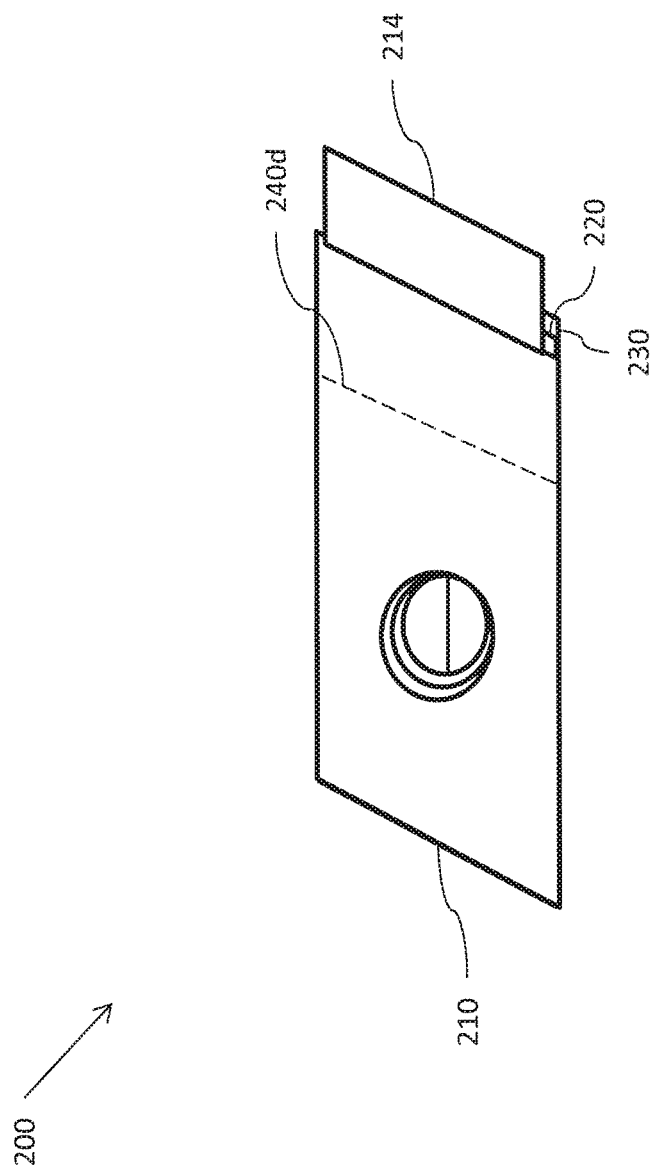
FIG. 2D is a line drawing illustrating the second example male incontinence pad at a further step of operation.
Figure 2E:
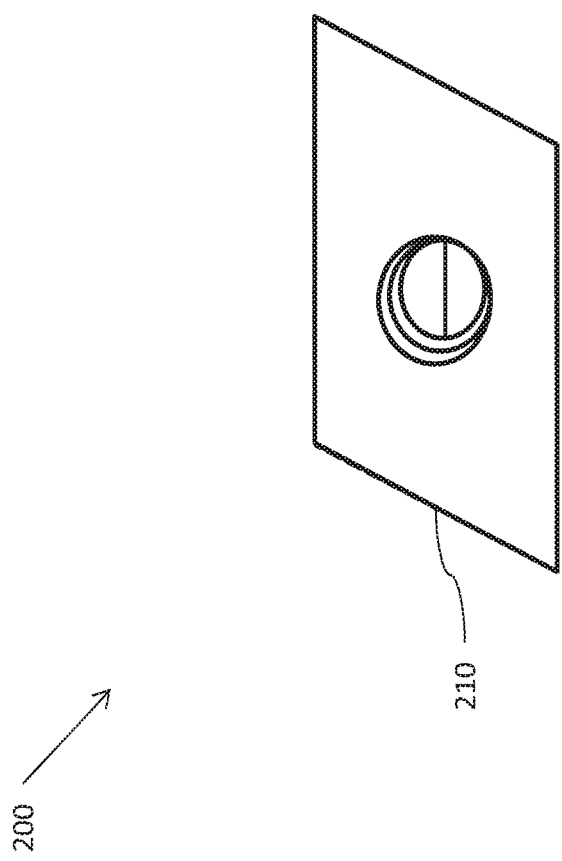
FIG. 2E is a line drawing illustrating the second example male incontinence pad at yet another step of operation.

FIGS. 1A-1B illustrate an example male incontinence pad 100. Among other things, pad 100 includes an outer absorbent pad 110, an inner lining 120, and an inner absorbent pad 130.

As illustrated, pad 100 is generally square. Pad 100 could have a variety of sizes (8"×8", 12"×12", 16×16", etc.). Pad 100 could also have other shapes (e.g., rectangular, oval, round, etc.) in other implementations.

Outer pad 110, lining 120, and inner pad 130 include apertures 112, 122, and 132, respectively, through which a male member may be inserted (extending from the outer surface of outer pad 110 to the other side of inner pad 130). As illustrated, apertures 112, 122, 132 are circular areas where material has been removed. Apertures 112, 122, 132 may typically between about 1-2" in length. In other implementations, apertures 112, 122, 132 may have other shapes (e.g., oval, rectangular, square, triangular, etc.). In certain implementations, apertures 112, 122, and 132 may be slits in the respective materials (e.g., cuts).

Outer pad 110 may be made of any appropriate absorbent material. In certain implementations, outer pad 110 may have components similar to those of the inner layers of diapers or feminine napkins.

In particular implementations, pad 110 may be composed of an outer permeable layer 180 and an inner absorbent layer 182. In certain implementations, the inner layer may be able to absorb about 200 times its own weight.

The inner layer could, for example, be made of cotton fibers or synthetic polymers. The inner layer could for, instance, be made of a hydrophilic polymer and a fibrous material such as wood pulp. The polymer could, for example, be made of fine particles of an acrylic acid derivative, such as sodium acrylate, potassium acrylate, or an alkyl acrylate. In certain implementations, the inner layer may be made of series 0570N700400 from Technical Absorbents Ltd. of North East Lincolnshire, York (UK).

The permeable layer may, for example, be made of a nonwoven fabric. Nonwoven fabrics are typically made from plastic resins, such as nylon, polyester, polyethylene, or polypropylene, and are assembled by mechanically, chemically, or thermally interlocking the plastic fibers. There are two primary methods of assembling nonwovens— the wet laid process and the dry laid process. A dry laid process, such as the "meltblown" method, is typically used to make nonwoven diaper fabrics. In this method, the plastic resin is melted and extruded, or forced, through tiny holes by air pressure. As the air-blown stream of fibers cools, the fibers condense onto a layer. Heated rollers are then used to flatten the fibers and bond them together. In certain implementations, the permeable layer may be made of polypropylene.

Lining 120 may be impermeable to liquid. Lining 120 may, for example, also be made of a nonwoven fabric, such as plastic resins made from nylon, polyester, polyethylene, or polypropylene. In certain implementations, lining 120 may be made of polyethylene.

Inner pad 130 may be made of any appropriate absorbent material. In certain implementations, inner pad 130 may have components similar to those of the inner layers of diapers or feminine napkins.

In particular implementations, inner pad 130 may be composed of an outer permeable layer 184 and an inner absorbent layer 186. The absorbent layer of pad 130 may be thinner than the absorbent layer of pad 110.

The inner layer could, for example, be made of cotton fibers or synthetic polymers. The inner layer could for, instance, be made of a hydrophilic polymer and a fibrous material such as wood pulp. The polymer could, for example, be made of fine particles of an acrylic acid derivative, such as sodium acrylate, potassium acrylate, or an alkyl acrylate. In certain implementations, the inner layer may be made of series 0150N704300 from Technical Absorbents Ltd. The permeable layer may be made of a nonwoven fabric.

Pad 110, lining 120, and pad 130 may be joined together by gluing, heating, or ultrasonic welding (e.g., along their periphery). In certain implementations, the periphery of the apertures 112, 122, 132 may also be joined so that the inner layers are sealed from the aperture.

In operation, the outer layer of outer pad 110 is positioned towards the wearer and moved to the groin area. The male member (i.e., penis) then is inserted through aperture 112, aperture 122, and aperture 132 (in the direction of arrow 102), and the pad is folded around the male member to make a pocket, primarily composed of inner pad 130.

For example, pad 100 may folded on one side towards the distal end of the male member and then the opposite side towards the distal end of the male member. This causes pad 130 to form a pocket (e.g., partial for full) for the distal end of the male member. The edges of the folded portions of pad 100 may be in proximity to each other or overlap each other. Pad 100 may then be folded along another side towards the distal end of the male member and then the opposite side towards the distal end of the male member, which will complete or reinforce the pocket for the male member. Portions of the pad from the third fold and from the fourth fold may be in proximity to each other or overlap each other. If desired, an incontinence brief may then be placed over the pad, which may better maintain the shape and/or position of pad 100.

In particular implementations, pad 110 may include a fastening system. The fastening system may, for example, include a first attachment zone and a second attachment zone. The attachment zones may, for instance, be parts of a hook-and-loop fastening system. In particular implementations, the attachment zones may be composed of a number of individual sections. In other implementations, the fastening system may include pins, snaps, and/or buttons.

During operation, the distal end of the male member should remain in the pocket formed by pad 130. Thus, if there is any discharge, pad 130 should absorb this. Moreover, lining 120 should prevent the discharge from reaching the wearer. If, however, the male member should come out from the pocket (e.g., due to movement or shrinkage), pad 110 should be able to assist in absorbing any discharge. The absorbency will typically not be as good as if the male member remained in the pocket, but the pad will usually absorb a substantial portion of the discharge. In particular implementations, the pad 110 and pad 130 may absorb about 1.5 liters in combination.

Pad 100 has a variety of features. For example, the pad may be able to substantially (or maybe even completely) absorb discharge from the wearer. Thus, when it is time to tend to the wearer, the task is much easier, as the pad may be removed simply and only minimal cleanup around the male member may be required. Moreover, a new pad may be readily fitted. When a wearer only uses a full-size incontinence brief, the entire brief must be changed, which requires a substantial amount of physical effort. Moreover, for individuals that require regular hydration (e.g., through a IV), this may mean that they need to be tended to every few hours. Having to change a full-size brief every few hours is a very labor intensive task. Additionally, the pad may prevent bed sores in the groin area due to the fact that the patient would not have to lie wet with urine for long periods of time in the region surrounding the entire groin area. This is especially true if the pad is being changed frequently, as it should be, which may be more likely since the changing process is greatly simplified. Moreover, the pad may cost quite a bit less than a typical incontinence brief, which may save the caregiver money. Another benefit is that wearers would not have to rely on catheters, which can cause quite a bit of pain and discomfort and can lead to urinary tract infections.

Although FIGS. 1A-1B illustrate an example male incontinence pad, other suitable male incontinence pads may have fewer, additional, or a different arrangement of components. For example, pad 110 may include a fastening system (e.g., one or more attachment zones). Moreover, an attachment zone may be placed on the inside of inner pad 130. Additionally, a different type of fastening system (e.g., pins) could be used. As another example, additional pads/layers could be used. In one example, inner pad 130 may have extra absorbency in the middle of the pad. Additionally, although four folds have been discussed for using the illustrated implementation, other modes of operation or implementations may allow for fewer or more folds.

In particular implementations, the liner 120 may have small apertures (e.g., slits) therein. These apertures may allow liquid to flow from the inner pad 110 to the outer pad 130. By allowing liquid to flow from the inner pad 110 to the outer pad 130, the apertures may assist in preventing leakage once the inner pad reaches its limit of absorption, by transferring the extra liquid into the outer pad. Additionally, the outer pad may include a wetness indicator, and the slits in the inner liner may allow the wetness indicator to function. Upon detecting wetness, the indicator may provide a visual signal (e.g., color change). The wetness indicator may, for example, operate using a pH zone (e.g., litmus).

FIGS. 2A-E illustrate another example male incontinence pad 200. Among other things, pad 200 includes an outer absorbent pad 210, an inner lining 220, and an inner absorbent pad 230. Pad 200 may have features similar to those for pad 100.

As illustrated, pad 200 is generally square. Pad 200 could also have other shapes (e.g., rectangular, oval, round, etc.) in other implementations.

Outer pad 210, lining 220, and inner pad 230 include apertures 212, 222, and 232, respectively, through which a male member may be inserted (extending from the outer surface of outer pad 210 to the other side of inner pad 230). As illustrated, apertures 212, 222, 232 are circular areas where material has been removed. Apertures 212, 222, 232 may typically be between about 1-2" in length. In other implementations, apertures 212, 222, 232 may have other shapes (e.g., oval, rectangular, square, triangular, etc.). In certain implementations, apertures 212, 222, 232 may be slits in the respective materials (e.g., cuts).

Outer pad 210 may be made of any appropriate absorbent material. In certain implementations, outer pad 210 may have components similar to those of the inner layers of diapers or feminine napkins.

In particular implementations, pad 210 may be composed of an outer permeable layer and an inner absorbent layer. The inner layer could, for example, be made of cotton fibers or synthetic polymers. The inner layer could for, instance, be made of a hydrophilic polymer and a fibrous material such as wood pulp. The polymer could, for example, be made of fine particles of an acrylic acid derivative, such as sodium acrylate, potassium acrylate, or an alkyl acrylate. In certain implementations, the inner layer may be made of series 0570N700400 from Technical Absorbents Ltd.

The permeable layer may, for example, be made of a nonwoven fabric. Nonwoven fabrics are typically made from plastic resins, such as nylon, polyester, polyethylene, or polypropylene, and are assembled by mechanically, chemically, or thermally interlocking the plastic fibers. There are two primary methods of assembling nonwovens—the wet laid process and the dry laid process. In certain implementations, the permeable layer may be made of polypropylene.

Lining 220 may be impermeable to liquid. Lining 220 may, for example, also be made of a nonwoven fabric, such as plastic resins made from nylon, polyester, polyethylene, or polypropylene. In certain implementations, lining 220 may be made of polyethylene.

Inner pad 230 may be made of any appropriate absorbent material. In certain implementations, inner pad 230 may have components similar to those of the inner layers of diapers or feminine napkins.

In particular implementations, inner pad 230 may be composed of an outer permeable layer and an inner absorbent layer. The inner layer could, for example, be made of cotton fibers or synthetic polymers. The inner layer could for, instance, be made of a hydrophilic polymer and a fibrous material such as wood pulp. The polymer could, for example, be made of fine particles of an acrylic acid derivative, such as sodium acrylate, potassium acrylate, or an alkyl acrylate. In certain implementations, the inner layer may be made of series 0150N704300 from Technical Absorbents Ltd. The permeable layer may be made of a nonwoven fabric.

Pad 210, lining 220, and pad 230 may be joined together by gluing, heating, or ultrasonic welding (e.g., along their periphery). In certain implementations, the periphery of the apertures 212, 222, 232 may also be joined so that the inner layers are sealed from the aperture.

As illustrated, pad 210 also includes a fastening system 213, which includes an attachment zone 214 and an attachment zone 216. Attachment zone 214 may, for example, include one part of a hook-and-loop fastening system, and attachment zone 216 may include the other part. Although shown as being continuous, attachment zones 214, 216 may be composed of a number of individual sections.

In operation, the outer layer of outer pad 210 is positioned towards the wearer and moved to the groin area. The male member then is inserted through aperture 212, aperture 222, and aperture 232 (in the direction of arrow 202), and the pad is folded along fold lines 240 around the male member to make a pocket 232.

Although fold lines are illustrated in FIGS. 2A-E, these may be for description only. That is, there may be no specifically prescribed lines along which to fold pad 200.

In the illustrated example, pad 200 is folded on one side, along fold line 240a, and then the opposite side, along fold line 240b. This causes pad 230 to form a pocket (e.g., partial for full) for the distal end of the male member. The edges of the folded portions of pad 200 may be proximate each other or overlap each other. Pad 200 is then folded along the side with attachment zone 216, along fold line 240c, and then the side with attachment zone 214, along fold line 240d, which completes or reinforces the pocket for the male member. Portions of the pad from the third fold and from the fourth fold may be proximate each other or overlap each other. Attachment zone 214 may then be coupled to attachment zone 216 so that the pad maintains its folded shape. If desired, an incontinence brief may then be placed over the pad, which may better maintain the shape and/or position of pad 200.

Although four folds are shown in the illustrated implementation, other modes of operation or implementations may allow for fewer of more folds.

During operation, the distal end of the male member should remain in the pocket formed by pad 230. Thus, if there is any discharge, pad 230 should absorb this. Moreover, lining 220 should prevent the discharge from reaching the wearer. If, however, the male member should come out from the pocket (e.g., due to movement or shrinkage), pad 210 should be able to assist in absorbing any discharge. The absorbency will typically not be as be as good as if the male member remained in the pocket, but the pad will usually absorb a substantial portion of the discharge.

Although FIGS. 2A-2E illustrate an example male incontinence pad, other suitable male incontinence pads may have fewer, additional, or a different arrangement of components. For example, pad 210 may not include attachment zone 214 and/or attachment zone 216. An attachment zone may, for example, be placed on the inside of inner pad 230. Additionally, a different type of fastening system (e.g., pins) could be used. As another example, additional pads/layers could be used. In one example, inner pad 230 may have extra absorbency in the middle of the pad.

Figure 3:
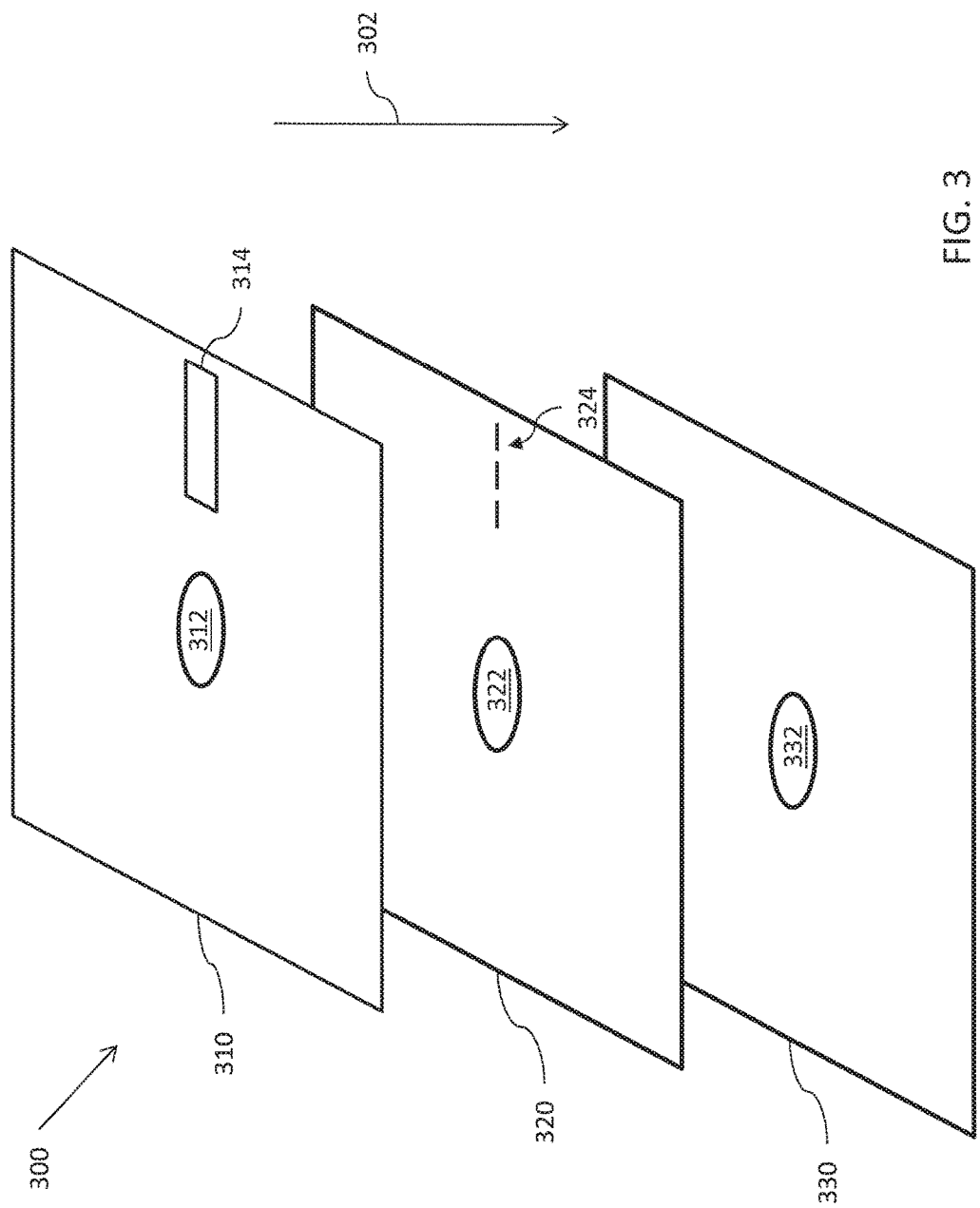
FIG. 3 is a line drawing illustrating an exploded view of a third example male incontinence pad.

FIG. 3 illustrates an additional example male incontinence pad 300. Among other things, pad 300 includes an outer absorbent pad 310, an inner lining 320, and an inner absorbent pad 330.

As illustrated, pad 300 is generally square. Pad 300 could also have other shapes (e.g., rectangular, oval, round, etc.) in other implementations.

Outer pad 310, lining 320, and inner pad 330 include apertures 312, 322, and 332, respectively, through which a male member may be inserted (extending from the outer surface of outer pad 310 to the other side of inner pad 330). As illustrated, apertures 312, 322, 332 are oval areas where material has been removed. Apertures 312, 322, 332 may typically be between about 1-2" in length. In other implementations, apertures 312, 322, 332 may have other shapes (e.g., circular, rectangular, square, triangular, etc.). In certain implementations, apertures 312, 322, and 332 may be slits in the respective materials (e.g., cuts).

Outer pad 310 may be made of any appropriate absorbent material. In particular implementations, pad 310 may be composed of an outer permeable layer and an inner absorbent layer.

Lining 320 may be impermeable to liquid. Lining 320 may, for example, also be made of a nonwoven fabric, such as plastic resins made from nylon, polyester, polyethylene, or polypropylene. In certain implementations, lining 320 may be made of polyethylene.

Inner pad 330 may be made of any appropriate absorbent material. In particular implementations, inner pad 330 may be composed of an outer permeable layer and an inner absorbent layer. The absorbent layer of pad 330 may be thinner than the absorbent layer of pad 310.

Pad 310, lining 320, and pad 330 may be joined together by gluing, heating, or ultrasonic welding (e.g., along their periphery). In certain implementations, the periphery of the apertures 312, 322, 332 may also be joined so that the inner layers are sealed from the aperture.

As illustrated, lining 320 includes a number of apertures 324 (e.g., slits) therein. If the apertures are slits, they may, for example, be approximately 0.25"-1.25" long. In particular implementations, the slits may be approximately 0.75" long. Apertures 324 allow liquid flow from the inner pad 330 to the outer pad 310. By allowing liquid to flow from the inner pad 330 to the outer pad 310, the apertures may assist in preventing leakage once the inner pad 330 reaches its limit of absorption, by conveying the extra liquid into the outer pad 310.

Outer pad 310 includes a wetness indicator 314. Wetness indicator 314 provides a visible indication (e.g., color change) when liquid is in outer pad 310, indicating that pad 300 is becoming full. The wetness indicator may, for example, use a pH technique (e.g., litmus) or any other appropriate technique.

In operation, the outer layer of outer pad 310 is positioned towards the wearer and moved to the groin area. The male member is then inserted through aperture 312, aperture 322, and aperture 332 (in the direction of arrow 302), and the pad is folded around the male member to make a pocket, primarily composed of inner pad 330.

For example, pad 300 may be folded on one side that does have the wetness indicator 314 and then another side that does not have the wetness indicator. This causes pad 330 to form a pocket (e.g., partial for full) for the distal end of the male member. The edges of the folded portions of pad 300 may be in proximity to each other or overlap each other. Pad 300 may then be folded along another side without the wetness indicator 314 and then along the side with the wetness indicator, resulting in the wetness indicator being visible when pad 300 is on the wearer. Portions of the pad from the third fold and from the fourth fold may be in proximity to each other or overlap each other.

In particular implementations, two or more edges may be fastened to each other so that that the pad maintains its folded shape. For example, two edges may be pinned to each other or an attachment zone on one edge may be coupled to attachment zone on another edge (e.g., by hook and loop fasteners). If desired, an incontinence brief may then be placed over the pad, which may better maintain the shape and/or position of pad 300.

During operation, the distal end of the male member should remain in the pocket formed by pad 330. Thus, if there is any discharge, pad 330 should absorb this. Moreover, lining 320 should prevent the discharge from reaching the wearer. If, however, the flow overwhelms the inner pad 330, the flow should leak into the outer pad 310 through apertures 324. Thus, outer pad 310 provides backup fluid capture. Pads 310, 330 may absorb about 1.5 liters in combination. Additionally, once enough fluid enters outer pad 300, wetness indicator 314 will activate, informing the wearer or a caretaker that it is time to change pad 300.

Pad 300 has a variety of features. For example, the pad may be able to substantially (or maybe even completely) absorb discharge from the wearer. Thus, when it is time to tend to the wearer, the task is much easier, as the pad may be removed simply and only minimal cleanup around the male member may be required. Moreover, a new pad may be readily fitted. When a wearer only uses a full-size incontinence brief, the entire brief must be changed, which requires a substantial amount of physical effort. Moreover, for individuals that require regular hydration (e.g., through a IV), this may mean that they need to be tended to every few hours. Having to change a full-size brief every few hours may be a very labor intensive task. Additionally, the pad may prevent bed sores in the groin area due to the fact that the patient would not have to lie wet with urine for long periods of time in the region surrounding the entire groin area. This is especially true if the pad is being changed frequently, as it should be, which may be more likely since the changing process is greatly simplified. Moreover, the pad may cost quite a bit less than a typical incontinence brief, which may save the caregiver money. Another benefit is that wearers would not have to rely on catheters, which can cause quite a bit of pain and discomfort and can lead to urinary tract infections.

Additionally, by allowing liquid to flow from the inner pad 330 to the outer pad 310, leakage may be prevented once the inner pad reaches its limit of absorption by absorbing the extra liquid in the outer pad. Furthermore, a wetness indication may be provided. These features may be used with other described incontinence pads.

Although FIG. 3, illustrates an example incontinence pad, other exemplary male incontinence pads may have fewer, additional, or a different arrangement of components. For example, a pad may have multiple attachment zones. Additionally, additional layers could be used. In one example, inner pad 330 may have extra absorbency in the middle of the pad.

Figure 4A:
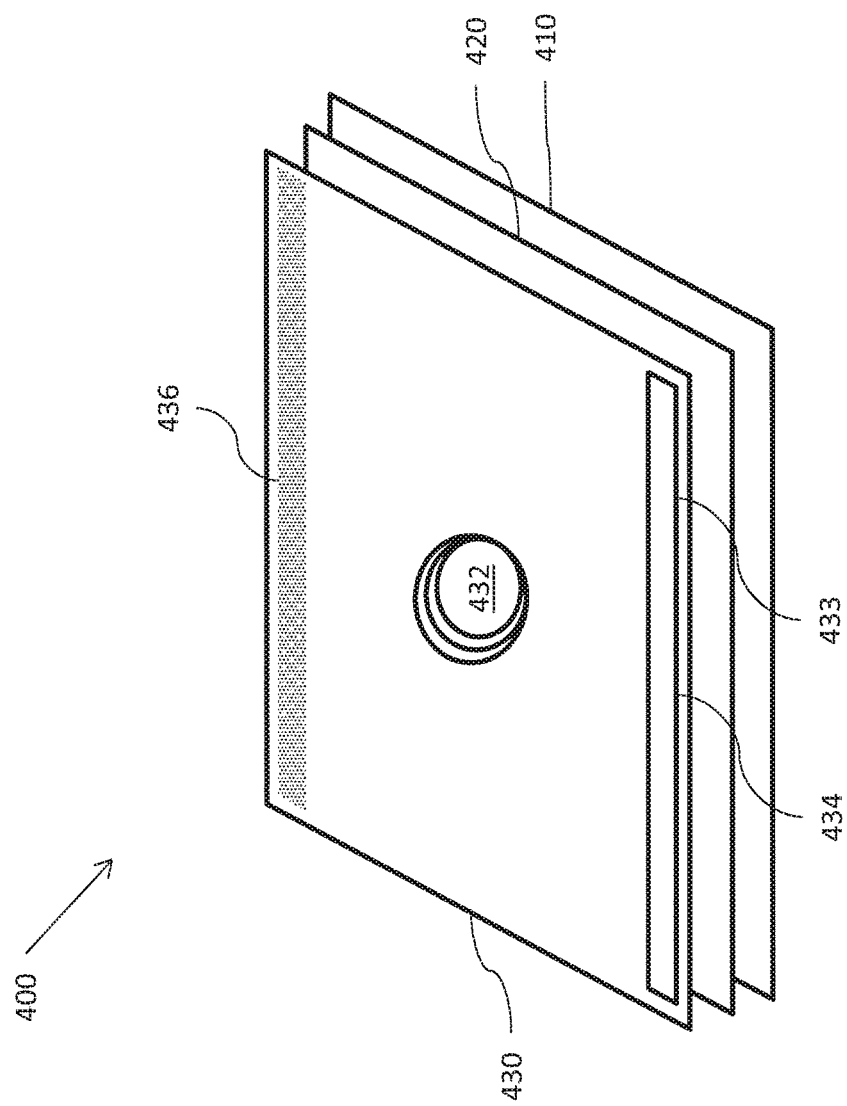
FIGS. 4A-4B are line drawings illustrating a fourth example male incontinence pad.
Figure 4B:
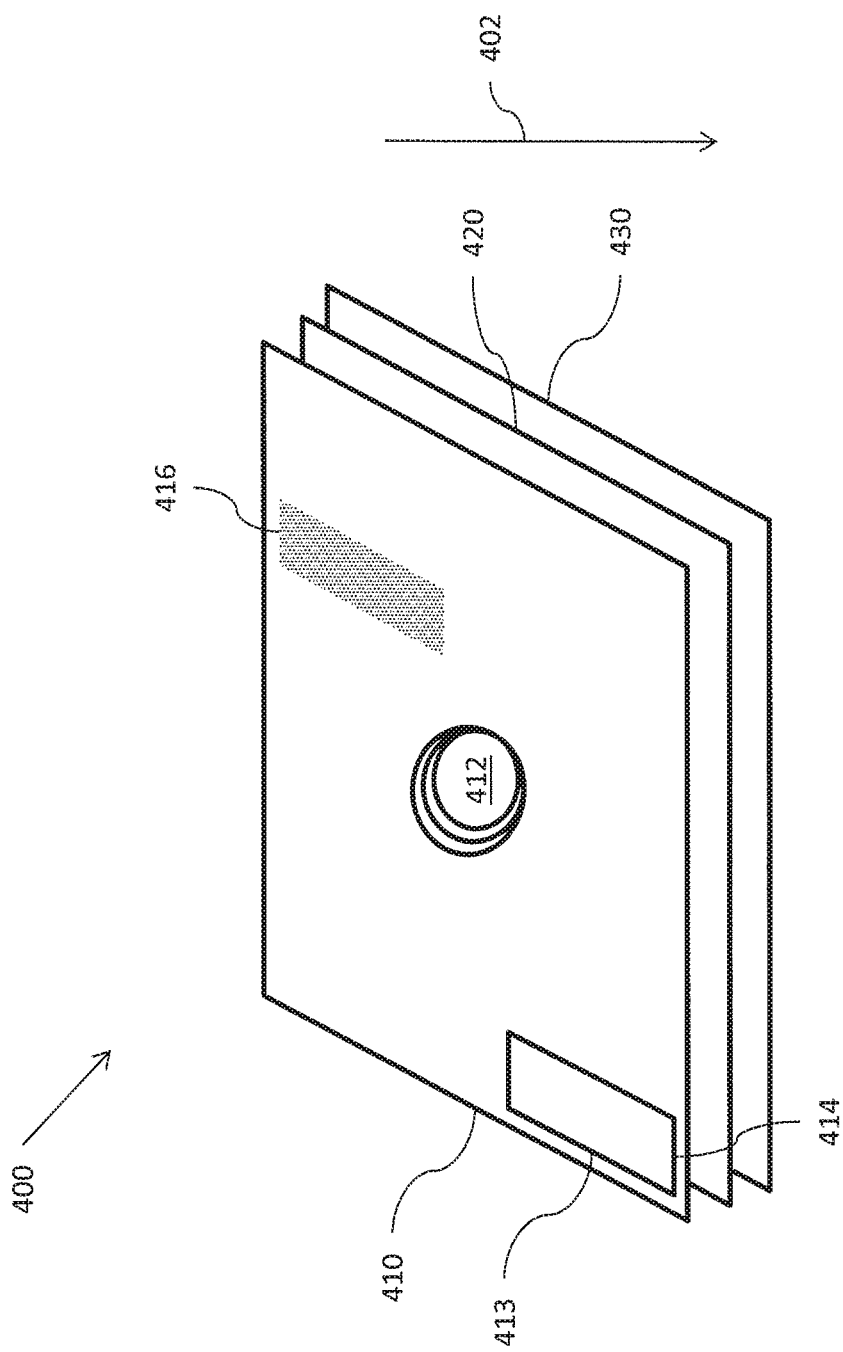

FIGS. 4A-4B illustrate another example male incontinence pad 400. Among other things, pad 400 includes an outer absorbent pad 410, an inner lining 420, and an inner absorbent pad 430.

As illustrated, pad 400 is generally square. Pad 400 could also have other shapes (e.g., rectangular, oval, round, etc.) in other implementations.

Outer pad 410, lining 420, and inner pad 430 include apertures 412, 422, and 432, respectively, through which a male member may be inserted (extending from the outer surface of outer pad 410 to the other side of inner pad 430). As illustrated, apertures 412, 422, 432 are circular areas where material has been removed. Apertures 412, 422, 432 may typically be between about 1-2" in length. In other implementations, apertures 412, 422, 432 may have other shapes (e.g., oval, rectangular, square, triangular, etc.). In certain implementations, apertures 412, 422, and 432 may be slits (e.g., cuts) in the respective materials.

Outer pad 410 may be made of any appropriate absorbent material. In particular implementations, pad 410 may be composed of an outer permeable layer and an inner absorbent layer. In certain implementations, the inner layer may be able to absorb about 200 times its own weight.

Lining 420 may be impermeable to liquid. Lining 420 may, for example, also be made of a nonwoven fabric, such as plastic resins made from nylon, polyester, polyethylene, or polypropylene. In certain implementations, lining 420 may be made of polyethylene.

Inner pad 430 may be made of any appropriate absorbent material. In particular implementations, inner pad 430 may be composed of an outer permeable layer and an inner absorbent layer. The absorbent layer of pad 430 may be thinner than the absorbent layer of pad 410.

Pad 410, lining 420, and pad 430 may be joined together by gluing, heating, or ultrasonic welding (e.g., along their periphery). In certain implementations, the periphery of the apertures 412, 422, 432 may also be joined so that the inner layers are sealed from the aperture.

As illustrated, pad 430 includes a fastening system 433, which includes an attachment zone 434 and an attachment zone 436. Attachment zone 434 may, for example, include one part of a hook-and-loop fastener system, and attachment zone 436 may include the other part. In particular implementations, attachment zone 434 and attachment zone 436 may be composed of a number of individual sections.

Additionally, pad 410 includes a fastening system 413, which includes an attachment zone 414 and an attachment zone 416. Attachment zone 414 may, for example, include one part of a hook-and-loop fastener system, and attachment zone 416 may include the other part. In particular implementations, attachment zone 414 and attachments zone 416 may be composed of a number of individual sections In operation, the outer layer of outer pad 410 is positioned towards the wearer and moved to the groin area. The male member is then inserted through aperture 412, aperture 422, and aperture 432 (in the direction of arrow 402). Pad 400 is then folded so that attachment zone 434 engages attachment zone 436, approximately folding pad 400 in half and establishing a partial pocket for the male member with pad 430. Then, the pad 400 is folded into approximately thirds in the other direction, with the section containing attachment zone 416 being folded first so that attachment zone 414 may engage it. This completes the pocket around the male member.

During operation, the distal end of the male member should remain in the pocket formed by pad 430. Thus, if there is any discharge, pad 430 should absorb this. Moreover, lining 420 should prevent the discharge from reaching the wearer. If, however, the male member should come out from the pocket (e.g., due to movement or shrinkage), pad 410 should be able to assist in absorbing any discharge. The absorbency will typically not be as good as if the male member remained in the pocket, but the pad will usually absorb a substantial portion of the discharge. In particular implementations, the two pads may absorb about 1.5 liters in combination.

Pad 400 has a variety of features. For example, the pad may be able to substantially (or maybe even completely) absorb discharge from the wearer. Thus, when it is time to tend to the wearer, the task is much easier, as the pad may be removed simply and only minimal cleanup around the male member may be required. Moreover, a new pad may be readily fitted. When a wearer only uses a full-size incontinence brief, the entire brief must be changed, which requires a substantial amount of physical effort. Moreover, for individuals that require regular hydration (e.g., through a IV), this may mean that they need to be tended to every few hours. Having to change a full-size brief every few hours may be a very labor intensive task. Additionally, the pad may prevent bed sores in the groin area due to the fact that the patient would not have to lie wet with urine for long periods of time in the region surrounding the entire groin area. This is especially true if the pad is being changed frequently, as it should be, which may be more likely since the changing process is greatly simplified. Moreover, the pad may cost quite a bit less than a typical incontinence brief, which may save the caregiver money. Another benefit is that wearers would not have to rely on catheters, which can cause quite a bit of pain and discomfort and can lead to urinary tract infections.

Although FIGS. 4A-4B illustrate an example incontinence pad, other exemplary male incontinence pads may have fewer, additional, or a different arrangement of components. For example, pad 410 may not include attachment zone 414 and/or attachment zone 416. An attachment zone may, for example, be placed on the inside of inner pad 430. Additionally, a different type of fastener (e.g., pins) could be used. As another example, additional pads/layers could be used. In one example, inner pad 430 may have extra absorbency in the middle of the pad. Additionally, although four folds have been discussed for the illustrated implementation, other modes of operation or implementations may allow for fewer of more folds.

In particular implementations, the liner 420 may have small apertures (e.g., slits) therein. These apertures may allow liquid to flow from the inner pad 410 to the outer pad 430. By allowing liquid to flow from the inner pad 410 to the outer pad 130, the apertures may assist in preventing leakage once the inner pad reaches its limit of absorption by leaking the extra liquid into the outer pad. Additionally, outer pad 410 may include a wetness indicator that activates in response to the liquid moving to the outer pad from the inner pad.

Figure 5:
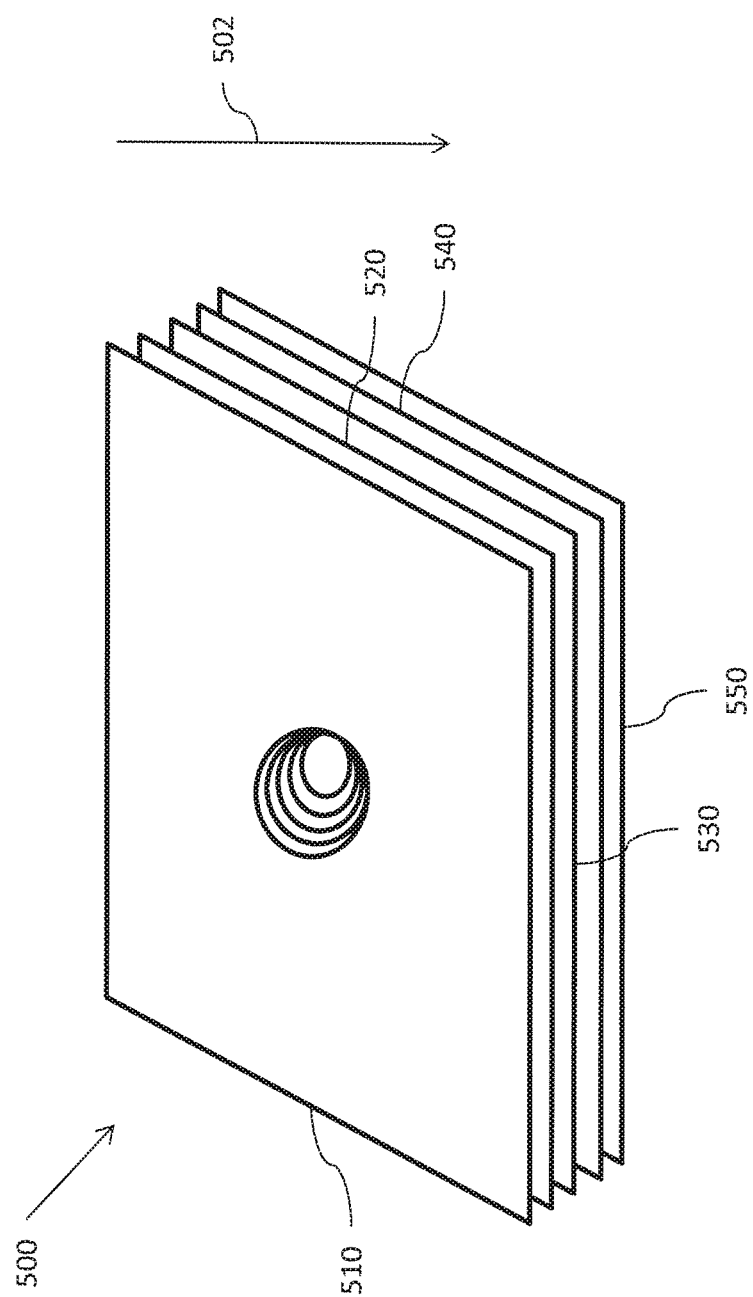
FIG. 5 is a line drawing illustrating a fifth example male incontinence pad.

FIG. 5 illustrates another example male incontinence pad 500. Among other things, pad 100 includes an outer permeable layer 510, an inner absorbent layer 520, an inner lining 540, an inner absorbent layer 540, and an outer permeable layer 550.

As illustrated, pad 500 is generally square. Pad 500 could also have other shapes (e.g., rectangular, oval, round, etc.) in other implementations.

Outer layer 510, inner layer 520, inner lining 530, inner layer 540, and outer layer 550 include apertures, respectively, through which a male member may be inserted (extending from the outer surface of outer layer 510 to the other side of outer layer 550). As illustrated, the apertures are circular areas where material has been removed. The apertures are typically between about 1-2" in length. In other implementations, the apertures may have other shapes (e.g., oval, rectangular, square, triangular, etc.). In certain implementations, the apertures may be slits in the respective materials (e.g., cuts).

The outer layer 510 and the inner layer 520 may form a pad. The pad may have components similar to those of the inner layers of diapers or feminine napkins.

The inner layer 520 could, for example, be made of cotton fibers or synthetic polymers. The inner layer could for, instance, be made of a hydrophilic polymer and a fibrous material such as wood pulp. The polymer could, for example, be made of fine particles of an acrylic acid derivative, such as sodium acrylate, potassium acrylate, or an alkyl acrylate. In certain implementations, the inner layer may be made of series 0570N700400 from Technical Absorbents Ltd.

The outer layer 510 may, for example, be made of a nonwoven fabric. In certain implementations, the permeable layer may be made of polypropylene.

Lining 530 may be impermeable to liquid. Lining 120 may, for example, also be made of a nonwoven fabric, such as plastic resins made from nylon, polyester, polyethylene, or polypropylene. In certain implementations, lining 120 may be made of polyethylene.

The outer layer 550 and the inner layer 540 may form a pad. The pad may have components similar to those of the inner layers of diapers or feminine napkins.

The inner layer could, for example, be made of cotton fibers or synthetic polymers. The inner layer could for, instance, be made of a hydrophilic polymer and a fibrous material such as wood pulp. The polymer could, for example, be made of fine particles of an acrylic acid derivative, such as sodium acrylate, potassium acrylate, or an alkyl acrylate. In certain implementations, the inner layer may be made of series 0150N704300 from Technical Absorbents Ltd. The inner layer 540 of pad 130 may be thinner than the inner layer 520. The outer layer 550 layer may be made of a nonwoven fabric.

Outer layer 510, inner layer 520, lining 530, inner layer 540, and outer layer 550 may be joined together by gluing, heating, or ultrasonic welding (e.g., along their periphery). In certain implementations, the periphery of the apertures of the layers may also be joined so that the inner layers are sealed from the aperture.

In operation, outer layer 510 is positioned towards the wearer and moved to the groin area. The male member then is inserted through the apertures (in the direction of arrow 502), and the pad is folded around the male member to make a pocket, primarily composed of outer layer 550.

For example, pad 500 may folded on one side towards the distal end of the male member and then the opposite side towards the distal end of the male member. This causes outer layer 550 to form a pocket (e.g., partial for full) for the distal end of the male member. The edges of the folded portions of the outer layer 550 may be in proximity to each other or overlap each other. Pad 500 may then be folded along another side towards the distal end of the male member and then the opposite side towards the distal end of the male member, which will complete or reinforce the pocket for the male member. Portions of the pad from the third fold and from the fourth fold may be in proximity to each other or overlap each other. If desired, an incontinence brief may then be placed over the pad, which may better maintain the shape and/or position of pad 500.

In particular implementations, outer layer 510 may include a fastening system. The fastening system may, for example, include a first attachment zone and a second attachment zone. The attachment zones may, for instance, be parts of a hook-and-loop fastening system. In particular implementations, the attachment zones may be composed of a number of individual sections. In other implementations, the fastening system may include pins, snaps, and/or buttons.

During operation, the distal end of the male member should remain in the pocket formed by outer 550. Thus, if there is any discharge, inner layer 5400 should absorb this. Moreover, lining 530 should prevent the discharge from reaching the wearer. If, however, the male member should come out from the pocket (e.g., due to movement or shrinkage), inner layer 520 should be able to assist in absorbing any discharge. The absorbency will typically not be as good as if the male member remained in the pocket, but the pad will usually absorb a substantial portion of the discharge. In particular implementations, the pad inner layer 520 and the inner layer 540 may absorb about 1.5 liters in combination.

Pad 500 has a variety of features. For example, the pad may be able to substantially (or maybe even completely) absorb discharge from the wearer. Thus, when it is time to tend to the wearer, the task is much easier, as the pad may be removed simply and only minimal cleanup around the male member may be required. Moreover, a new pad may be readily fitted. When a wearer only uses a full-size incontinence brief, the entire brief must be changed, which requires a substantial amount of physical effort. Moreover, for individuals that require regular hydration (e.g., through a IV), this may mean that they need to be tended to every few hours. Having to change a full-size brief every few hours is a very labor intensive task. Additionally, the pad may prevent bed sores in the groin area due to the fact that the patient would not have to lie wet with urine for long periods of time in the region surrounding the entire groin area. This is especially true if the pad is being changed frequently, as it should be, which may be more likely since the changing process is greatly simplified. Moreover, the pad may cost quite a bit less than a typical incontinence brief, which may save the caregiver money. Another benefit is that wearers would not have to rely on catheters, which can cause quite a bit of pain and discomfort and can lead to urinary tract infections.

Although FIG. 5 illustrates an example male incontinence pad, other suitable male incontinence pads may have fewer, additional, or a different arrangement of components. For example, outer layer 510 may include a fastening system (e.g., one or more attachment zones). Moreover, an attachment zone may be placed on the outer layer 550. Additionally, a different type of fastening system (e.g., pins) could be used. As another example, additional pads/layers could be used. In one example, inner layer 540 may have extra absorbency in the middle of the pad. Additionally, although four folds have been discussed for using the illustrated implementation, other modes of operation or implementations may allow for fewer or more folds.

In particular implementations, the liner 530 may have small apertures (e.g., slits) therein. These apertures may allow liquid to flow from the inner layer 540 to the inner layer 520. By allowing liquid to flow from the inner layer 540 to the inner layer 520, the apertures may assist in preventing leakage once the inner pad reaches its limit of absorption, by transferring the extra liquid into the outer pad. Additionally, the outer layer 510 may include a wetness indicator, and the slits in the inner liner may allow the wetness indicator to function. Upon detecting wetness, the indicator may provide a visual signal (e.g., color change). The wetness indicator may, for example, operate using a pH zone (e.g., litmus).

The pads discussed herein has mainly been discussed with respect to adults, but they may also be useful for males of other ages (e.g., boys). In general, the pads may be useful for any male who happens to be in a setting (e.g., hospital, nursing home, or home care) and are in briefs (diapers) and unable to care for their private need of urinating on their own.

Although the invention has been described with reference to specific implementations, this description is not meant to be construed in a limiting sense. On the contrary, various modifications of the disclosed implementations will be readily apparent to those skilled in the art upon reference to the written description and drawings. The scope of the protected subject matter should therefore be judged based on the following claims, which may encompass one or more aspects of one or more implementations.

The invention claimed is:

1. A male incontinence pad for use by a male wearer the male incontinence pad comprising:

a first absorbent pad including an aperture;

a second absorbent pad including an aperture; and a liquid impermeable lining between the pads, the lining including an aperture;

wherein the apertures through the first absorbent pad, the second absorbent pad, and the lining are aligned to allow a male member to be placed therethrough, and the second absorbent pad is adapted to be folded to form a pocket for the male member; and wherein the second absorbent pad operates to absorb any liquid discharge from the male member and the liquid impermeable liner operates to prevent the liquid discharge from reaching the wearer; and wherein the first absorbent pad operates to cooperate with the second absorbent pad to absorb any liquid discharge if the male member is not within the pocket.

2. The pad of claim 1, wherein the first absorbent pad and the lining are adapted to fold with the second absorbent pad.

3. The pad of claim 2, further comprising a fastening system to maintain the first absorbent pad, the second absorbent pad, and the lining in the folded position.

4. The pad of claim 1, wherein the first absorbent pad includes a liquid permeable outer layer and an absorbing inner layer.

5. The pad of claim 1, wherein the second absorbent pad includes a liquid permeable outer layer and an absorbing inner layer.

6. The pad of claim 1, wherein the water impermeable lining includes a number of apertures therein to allow liquid to pass from the second absorbent pad to the first absorbent pad.

7. The pad of claim 6, wherein the first absorbent pad includes a wetness indicator on the exterior thereof, the wetness indicator providing a visible indication of when wetness has traversed the apertures.

8. A male incontinence pad comprising:

a first liquid permeable outer layer;

a first absorbing layer next to the first liquid permeable outer layer;

a liquid impermeable layer next to the first absorbing layer;

a second adsorbing permeable layer next to the liquid impermeable layer; and a second liquid permeable layer next to the second absorbing layer;

wherein each layer has an aperture through it and is adapted to be folded so that the second liquid permeable layer forms a pocket;

wherein the pad further comprises a fastening system to maintain the layers in the folded position;

wherein the liquid impermeable lining includes a number of apertures therein to allow liquid to pass from the second absorbent layer to the first absorbent layer; and wherein the first absorbent layer includes a wetness indicator on the exterior thereof, the wetness indicator providing a visible indication of then wetness has traversed the apertures.

9. A male incontinence pad comprising:

an outer pad having an outer permeable layer and an inner absorbent layer;

an inner pad having an outer permeable layer and an inner absorbent layer; and a liquid impermeable lining positioned between the outer pad and the inner pad;

wherein the outer pad, the inner pad and the liquid impermeable lining are joined together and each having an aperture;

wherein the apertures are aligned and adapted to receive a male member;

wherein the outer pad, the liquid impermeable lining and the inner pad are adapted to be folded to form a pocket for the male member;

wherein the male incontinence pad further comprises a fastening system for maintaining the pocket; and wherein the liquid impermeable lining includes apertures effective for allowing liquid to flow from the inner pad to the outer pad.

* * * * *